United States Patent
Soeda et al.

(10) Patent No.: US 6,878,183 B2
(45) Date of Patent: Apr. 12, 2005

(54) SUBLIMATION PURIFYING METHOD AND APPARATUS

(75) Inventors: Mahito Soeda, Fukuoka (JP); Shuhei Hotta, Osaka (JP); Kazuo Ishii, Fukuoka (JP)

(73) Assignees: Nippon Steel Chemical Co., Ltd., Tokyo (JP); Osaka Yuka Industries Co., Ltd., Osaka (JP)

(*) Notice: Subject to any disclaimer, the term of this patent is extended or adjusted under 35 U.S.C. 154(b) by 218 days.

(21) Appl. No.: 10/239,064

(22) PCT Filed: Mar. 19, 2001

(86) PCT No.: PCT/JP01/02173
§ 371 (c)(1),
(2), (4) Date: Sep. 19, 2002

(87) PCT Pub. No.: WO01/70364
PCT Pub. Date: Sep. 27, 2001

(65) Prior Publication Data
US 2003/0030193 A1 Feb. 13, 2003

(30) Foreign Application Priority Data
Mar. 23, 2000 (JP) ........................ 2000-82195

(51) Int. Cl.$^7$ .................................. B22F 1/00
(52) U.S. Cl. .................. 75/255; 266/172; 266/202
(58) Field of Search .............. 266/172, 200, 266/202; 75/255

(56) References Cited

U.S. PATENT DOCUMENTS

| 3,764,272 A | * | 10/1973 | Sterling ................. 422/244 |
| 5,131,634 A | | 7/1992 | Abodishish et al. .......... 266/91 |
| 5,338,518 A | | 8/1994 | Marion et al. ............. 422/211 |
| 6,583,583 B1 | * | 6/2003 | Soeda et al. ............. 315/169.3 |

FOREIGN PATENT DOCUMENTS

| GB | 510196 A1 | 7/1939 |
| GB | 536821 A1 | 5/1941 |
| GB | 552234 A1 | 3/1943 |
| GB | 962166 A1 | 7/1964 |
| JP | H05-043203 | 2/1993 |
| JP | H06-263438 | 9/1994 |
| JP | H07-024205 | 1/1995 |
| JP | H09-103602 | 4/1997 |
| JP | 2000-093701 | 4/2000 |

OTHER PUBLICATIONS

English language translation of JP 09103602 A, Apr. 22, 1997.*
Supplementary European Search Report dated Apr. 9, 2003.
International Search Report for PCT/JP01/02173 mailed on Jul. 3, 2001.
Translation of International Preliminary Examination Report mailed on Aug. 6, 2002.

* cited by examiner

Primary Examiner—Scott Kastler
(74) Attorney, Agent, or Firm—Rader, Fishman & Grauer PLLC

(57) ABSTRACT

This invention relates to a method for sublimation refining which gives a high-purity product in high yield while preventing corrosion of the apparatus, contamination of the product and change in quality of the product and to an apparatus useful for the method. The apparatus of this invention for sublimation refining comprises a heat generating unit made of a material generating heat by electromagnetic induction, sublimating unit A and collecting units B and C, respectively independently controllable in temperature by electromagnetic induction heating and the inner surface or the inner tube of the sublimating or collecting unit is made of a material like metal and ceramic inert to sublimable substances. According to the method of this invention for sublimation refining, a sublimable substance is introduced to sublimating unit A, the sublimating unit is heated by electromagnetic induction thereby sublimating the sublimable substance, the sublimate is introduced to collecting unit B containing a zone controlled in temperature by electromagnetic induction heating and the object sublimable substance is collected.

10 Claims, 1 Drawing Sheet

SUBLIMATION PURIFYING METHOD AND APPARATUS

FIELD OF TECHNOLOGY

This invention relates to a method for sublimation refining and to an apparatus for sublimation refining useful for said method.

BACKGROUND TECHNOLOGY

It is known that any solid which sublimates without decomposition at normal pressure or under reduced pressure can in principle be refined by sublimation at suitable temperature and pressure; in actuality, because of a low rate of sublimation and poor refining efficiency, sublimation refining has been applied only to a limited number of solids. However, sublimation refining is useful for refining solids which are difficult to refine by distillation or recrystallization and particularly useful for refining compounds which start to decompose in a high temperature region. Some of apparatuses for such sublimation refining are disclosed in JP6-263438 A and JP7-24205 A.

Apparatuses for sublimation refining are divided by shape into such types as vertical and horizontal or by process into such types as gas entraining and vacuum. A suitable combination of these types provides a variety of apparatuses for sublimation refining and a proper selection of apparatuses is made in consideration of the properties of the sublimable substance to be refined such as thermal stability, vapor pressure and ease of vaporization, the throughput and the yield and purity of the object substance.

In case the amount of a solid to be refined is relatively large, however, it is difficult to sublimate the solid in a short time by heating in any of the aforementioned conventional apparatuses for sublimation refining and the solid shows an increasing possibility of decomposing or changing in property in the meantime. Moreover, precise control of the temperature in the sublimating and collecting units within a certain range becomes difficult to exercise and, as a result, the solid not only decomposes or changes in property but also does not improve sufficiently in purity.

When a metallic material such as ferrous metal is used as a structural material in an apparatus for sublimation refining, it becomes a matter of concern that a sublimable substance or impurities contained therein may react with the metal or may change in quality by the catalytic action of the metal. The reaction product or the product with changed quality, if any, contaminates the refined substance. In particular, trace metals exert great influences on the properties of metal complexes and it is important to prevent contamination of the refined substance.

DISCLOSURE OF THE INVENTION

Accordingly, an object of this invention is to provide a method and an apparatus for sublimation refining which is capable of heating a raw material supplied in small or large amounts uniformly in a short time under precise control of the heating temperature thereby sublimating and refining a solid material of poor thermal stability efficiently in high purity.

This invention relates to an apparatus for sublimation refining which comprises a heating unit made of a material generating heat by electromagnetic induction, a sublimating unit and a collecting unit and the temperature of each of the sublimating and collecting units can be controlled independently by electromagnetic induction heating. The apparatus is characterized by that the inner surface or the inner tube of the sublimating unit and/or the collecting unit contacting a sublimable substance is made of a material inert to said sublimable substance such as metal, ceramic, glass and resin.

Moreover, this invention relates to a method for sublimation refining by the use of an apparatus for sublimation refining which comprises a heating unit made of a material generating heat by electromagnetic induction, a sublimating unit and a collecting unit wherein the temperature of the sublimating unit and the collecting unit can be controlled independently by electromagnetic induction heating and the inner surface or the inner tube of the sublimating unit and/or the collecting unit contacting a sublimable substance is made of a material inert to said sublimable substance such as metal, glass and ceramic and the method comprises introducing a sublimable substance to the sublimating unit of the apparatus for sublimation refining, heating the sublimating unit by electromagnetic induction thereby sublimating said sublimable substance, introducing the sublimate to the collecting unit containing a zone controlled in temperature by electromagnetic induction heating and collecting the object sublimable substance.

The apparatus of this invention for sublimation refining has a sublimating unit and a collecting unit and each of the two units has a heat generating unit which can be independently controlled in temperature and generates heat by electromagnetic induction heating. There is no restriction on the shape of the units as long as the inner surface which comes into contact with a sublimable substance is made of a material inert to said sublimable substance; for example, the sublimating unit is shaped like a tube or a flask and the collecting unit is shaped like a tube or a coil.

The heat generating unit is made of a material which generates heat by electromagnetic induction. If this material is inert to sublimable substances and possesses the specified strength and moldability, this material alone would suffice; if not, the material is made of two layers or more with an inert material forming the inner layer or an inner tube made of an inert material is fitted in. Ordinarily, a ferrous material is an excellent heat generator by electromagnetic induction and also shows good strength and moldability. Therefore, a ferrous metal is advantageous as a material for making the heat generating unit, but on account of its shortcoming as a well-known contaminant of sublimable substances, it is preferable to apply a combination of a ferrous metal and an inert material.

A material inert to sublimable substances means that the material in question does not react with sublimable substances under the conditions of sublimation refining; furthermore, the inertness here has a broader meaning to the effect that the material does not react with compounds resulting from the decomposition of sublimable substances during sublimation refining, the material does not act as a catalyst for the decomposition of sublimable substances nor for the reaction of sublimable substances with other components, the material does not contaminate the refined sublimable substance and the material does not react with an enveloping gas such as oxygen while the apparatus is in operation or out of service. For example, when a metal rusts by oxidation and physically comes off to contaminate the refined sublimable substance, the metal cannot be said inert to sublimable substances; however, slight contamination of the refined sublimable substance to such an extent as to present no problem in practical use is tolerated. Normally, noble metals such as gold and platinum, glass, ceramic and fluoropolymers are available as materials of the aforementioned kind, although they vary with the kind of sublimable substances.

The collecting unit is provided on the downstream side of the sublimating unit and is heated to the specified temperature below the solidification point. In order to prevent any component other than the object sublimable substance from solidifying together, it is advisable to provide a zone for collecting the object sublimable substance and control the temperature there within the specified range. It is also advantageous to provide plural zones differing in temperature from one another and establish a temperature gradient between the sublimating and collecting units while allowing the temperature to drop approximately stepwise towards the downstream side.

An inductive coil is provided in the periphery of the sublimating and collecting units for the purpose of causing the heating material to generate heat by electromagnetic induction.

There is no particular restriction on sublimable substances to be refined by the method of this invention. The method is particularly effective for refining solid materials which show the possibility of decomposing or changing in quality (including transformation of crystal form) near the sublimation temperature, for example, for solid materials useful as electrical and electronic materials and optical materials such as luminous substances in which the presence of impurities in trace amounts or the difference in or transformation of crystal form exerts a great influence. Their examples include materials for electroluminescence devices and semiconductor devices. The method is particularly effective for refining materials for electroluminescence devices and semiconductor devices based on metal complexes such as an aluminum-quinoline complex. However, the method is not limited to the aforementioned materials and is naturally applicable to sublimable solid materials for ordinary use such as pyromellitic dianhydride, carbazole, pyrene and anthraquinone.

Some of the aforementioned sublimable substances may react with the metallic material of which the apparatus for sublimation refining is made, suffer change in property by the catalytic action of the metal or become contaminated with impurities originating from the metal. For this reason, it is preferable to prevent contamination by coating the inner surface with an inert material, fitting in an inner tube or using an inert material such as magnetic ceramic as a heating element.

An acceptable type of apparatus for electromagnetic induction heating is the one which generates heat by passing a high-frequency alternating current through a coil provided around the heating material. The frequency of the current to be supplied to the apparatus is generally 50–500 Hz and the commercially available frequency presents no problem.

PREFERRED EMBODIMENTS OF THE INVENTION

Figure 1:
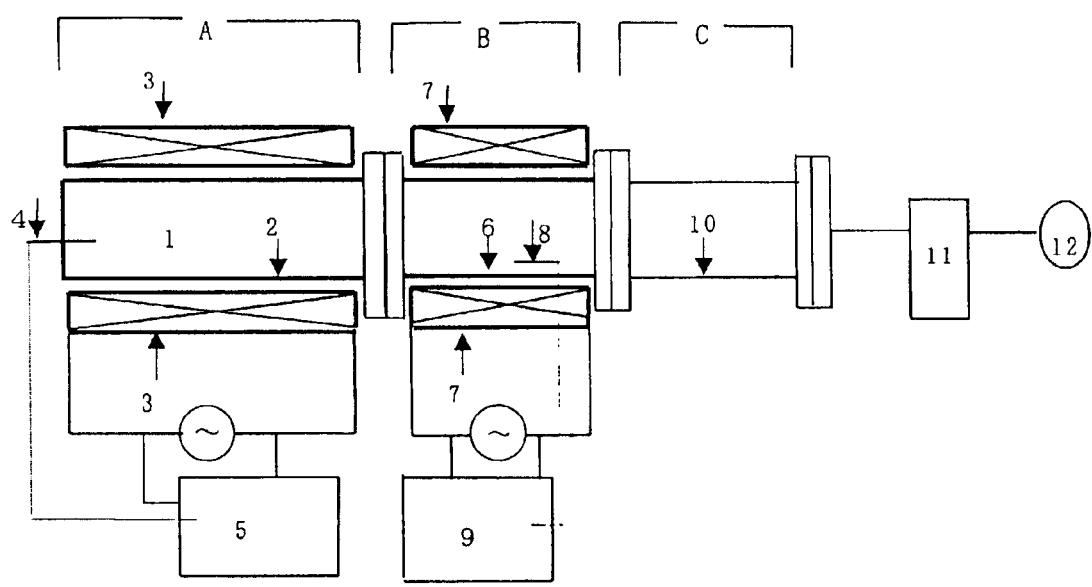
FIG. 1 is a cross section of an example of the apparatus for practicing the method of this invention for refining sublimable substances and the apparatus comprises of sublimating unit A, collecting unit B and collecting unit C, each tubular in shape and connected in series.

This invention will be described below with reference to the drawing. For the sake of simplicity, a material which is inert to sublimable substances is referred to as "an inert material" and a material which generates heat by electromagnetic induction is referred to as "a heating material."

This apparatus for sublimation refining is tubular, may be varied in diameter and cross-sectional shape midway if necessary, and has a sublimating unit upstream and collecting units downstream in the direction of the flow of a sublimable substance to be refined. The tubes in the sublimating unit and at least in a part of the collecting units are made of a heating material to allow heating by electromagnetic induction and a coil is provided around the heating material.

Sublimating unit A forms a sublimating chamber in the inside and is provided with a tube 2 made of a heating material, an induction coil 3 surrounding the tube 2, a thermocouple 4 and a temperature controller 5. The temperature controllers 5 and 9 are connected with an alternating current source, converts the current into a high-frequency current and supply the output to the induction coils 3 and 7 while the supply of electric power can be controlled by the signals from the thermocouples 4 and 8.

The tube 2 is made of a heating material, but it is allowable to use a heating material together with other materials. The heating material here is either metallic or nonmetallic, but it is preferably an electrically conductive magnetic material. It does not matter whether the tube 2 is made of two layers or more of a metallic material or it is a combination of one layer of a metallic material and an inner layer or an inner tube of an inert material. In this case, however, at least one layer needs to be a heating material.

A solid material to be refined may be introduced to the sublimating chamber continuously in the form of powder, but it is simpler to introduce the solid material intermittently while placing the material in a specimen container such as a boat. In case the solid material tends to change in quality by heat, it is introduced continuously or intermittently in small portions Heating is carried out by electric power and the supply of electric power is controlled in such a manner as to minimize the time required to reach the sublimation temperature. Lowering the heat capacity is effective for raising the rate of temperature rise and it is advantageous not to make the diameter and wall thickness greater than is necessary. Moreover, it is advantageous to make the whole of tube 2 the heat generating unit.

On the downstream side of sublimating unit A is provided a collecting unit which is kept lower in temperature than the sublimating unit. The collecting unit preferably contains plural zones and at least one of the zones can be heated by electromagnetic induction. In the drawing are shown two zones, that is, collecting unit B which is equipped with a device for induction heating and collecting unit C which is not. Collecting unit B is connected by means of a flange with sublimating unit A. Collecting unit B is made of a tubular, electrically conductive magnetic material and it does not matter whether the tube 6 is made of two layers of more of a metallic material, made of at least one layer of a metallic material and another nonmetallic material or made of a combination of one layer of a metallic material and an inner layer or an inner tube of an inert material. However, at least one layer needs to be a heating material, preferably an electrically conductive magnetic material. The heating device for collecting unit B can be made similar to that for sublimating unit A. Collecting unit B is connected with collecting unit C on the downstream side.

The drawing shows that collecting unit C consists of a tube 10 and its periphery may be kept warm, cooled or left in contact with air. Unlike the drawing, collecting unit C may be placed on the upstream side of collecting unit B. Collecting unit B which can be heated by electromagnetic induction may be made in one stage or in two stages or more and, in case one kind of substance is to be collected, it is allowable to adopt an arrangement so that only the portion intended for collection can be heated by magnetic induction.

Collecting unit B which can be heated by magnetic induction is operated advantageously by controlling its temperature in such a manner as to collect the object substance with a purity higher than the specified value and by maintaining a zone of constant temperature over the specified length. That is, from the sublimating unit to the collecting unit, there are two or more zones which are kept at roughly constant temperature by magnetic induction heating and the temperature is allowed to drop successively towards the downstream side. The outlet of the collecting unit on the most downstream side is connected, through a gas takeout tube and a trap 11, with a vacuum pump 12.

The method for refining a sublimable substance containing impurities by the use of the aforementioned apparatus for sublimation refining will be explained below. For convenience' sake, the explanation is given to the case where the solid raw material contains the object sublimable substance and sublimable impurities of lower sublimation temperature.

When a solid raw material is introduced to sublimating unit A of the apparatus for sublimation refining illustrated in FIG. 1 and an alternating current is passed from the power source to the induction coil 3, the tube 2 made of a heating material in sublimating unit A generates heat by electromagnetic induction heating and the raw material reaches the sublimation temperature. The sublimation temperature is below the boiling point; it may be above or below the melting point but it is necessarily the temperature which gives the specified vapor pressure. Normally, this vapor pressure is in the range of $1 \times 10^{-6}$–700 Torr (approximately 0.13 mPa–93 kPa). The temperature of the tube 2 is controlled at the set temperature by measuring the temperature inside sublimating unit A with the aid of the thermocouple 4 and turning on or off the current source by the temperature controller 5 or by inverter control. The sublimable substance in the raw material introduced to sublimating unit A sublimates and the sublimated gas moves towards collecting unit B dragged by suction of the vacuum pump 12 located at the rear of collecting unit C. The non-sublimable impurities contained in the raw material remains as residue at the bottom of sublimating unit A.

The sublimated gas moving into collecting unit B is cooled in the tube 6 which is kept at a temperature below the melting point of the object sublimable substance and above the solidification point of the principal impurities in the sublimated gas and the object substance alone condenses and solidifies on the inner surface of the tube 6. Heat generation and temperature control in collecting unit B can be effected as in sublimating unit A. This temperature is preferably above the dew point of the impurities and as low as possible. In case a large number of impurities are present and contamination by trace amounts of such impurities is tolerable, the temperature can be set at a still lower level. Upon completion of sublimation refining, the object sublimable substance is recovered by dismantling collecting unit B.

The tubes making up the sublimating and collecting units of the apparatus of this invention for sublimation refining generate heat by electromagnetic induction heating and the materials for the tubes are metallic or nonmetallic as a whole or only in those parts which generate heat or the materials are composed of two layers or more at least one of which is a heating material.

Preferable heating materials are generally ferrous metals such as iron and iron alloys and it is possible to use stainless steel, graphite and magnetic ceramics such as titanium nitride from the viewpoint of securing heat resistance and anticorrosion.

When a heating material is a metal such as iron, the material is often not inert to sublimable substances and oxygen gas. In a case such as this, the inner layer is made of an inert material or an inner tube made of an inert material is fitted in.

Inert materials include metals such as noble metals and alloys, heat-resistant resins such as fluoropolymers, polyimides and silicones, glasses such as quartz glass, Pyrex, hard glass and enamel and ceramics such as alumina, silicon nitride and porcelain. Preferable inert materials are metals, glasses such as enamel, fluoropolymers and ceramics. Of these materials, those which lack strength or are difficult to mold or expensive can be made into an inner layer by such means as vapor deposition in thin film and plating.

It is advantageous to use as an inner layer a magnetic ceramic such as titanium nitride which is a heating material as well as an inert material. Furthermore, in place of a multilayer structure, a single layer of a material which is a heating material as well as an inert material such as SiC, graphite and titanium nitride is used to make the sublimating and collecting units.

As for the material for the inner surface or the inner tube which comes into contact with sublimable substances, an inert material other than the commonly used metallic materials is advantageous in the following cases.

(1) Sublimation Refining of Metal Complexes

When the metal in a metal complex comes into contact with a metal of a different kind at high temperature, exchange of metal takes place at a certain rate. As a result, the purity of the metal complex drops and, in some cases, drops lower than that of the raw material. Also, proper selection of a packing material for maintaining airtightness is as important as selection of a structural material for the apparatus. For example, due to an advance in high vacuum technology, a variety of metallic or metal-coated packing materials have recently come into practical use. Metal complexes mostly decompose to some extent when subjected to sublimation refining at high temperature. The ligand formed in the decomposition forms a complex upon contact with a metallic material of a different kind.

(2) Sublimation Refining of Organic Compounds

Carboxylic acid anhydrides are sublimable and carboxylic acids resulting from the anhydrides by absorption of moisture and ring opening often show strong corrosiveness against metals. Those compounds which are capable of forming complexes such as 8-hydroxyquinoline, phthalic acid and pyromellitic acid form complexes on the surface in contact with metals, possibly damaging the apparatus and contaminating the refined product. When an apparatus made of a metallic material is used for refining the object compound containing acids, sulfur compounds and halogen compounds, which is the case with a component derived from coal tar, these impurities may corrode the metal, decompose by the catalytic action of the metal and contaminate the product by the decomposition products.

The induction coils 3 and 7 and the temperature controllers 5 and 9 used for electromagnetic induction heating of the tubes 2 and 6 can be served satisfactorily by those which have been used in known apparatuses for electromagnetic induction heating. It is important to place the induction coils 3 and 7 on the periphery of the tubes 2 and 6 over the specified length in order to realize uniform heating of the tubes.

Generation of heat in the tubes 2 and 6 by electromagnetic induction heating can generate heat uniformly in sublimating unit A and a certain zone of collecting unit B and this contributes to realize a higher rate of temperature rise, for example, on the order of several minutes to 60 minutes from room temperature to 400° C., and greater precision in temperature control.

Only the object sublimable substance is condensed and collected in collecting unit B while the impurities in the raw material are allowed to pass there as gas and condensed and collected in collecting unit C which is connected directly with collecting unit B. Therefore, it suffices to equip collecting unit C with a common cooling device such as air cooling and liquid cooling capable of cooling to the specified temperature, for example, room temperature.

It is desirable to provide a temperature gradient dropping approximately stepwise towards the downstream side through sublimating unit A, collecting unit B and collecting unit C in order to enhance the purity of the object product and raise the yield of recovery. Stepwise here means the existence of plural zones, each kept nearly constant in temperature, in the direction of gas stream in the apparatus for sublimation refining. This does not exclude the existence of a zone in which the temperature drops continuously. The length of a zone in which the temperature is kept nearly constant is determined from the viewpoint of securing a capacity to collecting the product of constant composition.

Reduction of the pressure inside the refining apparatus lowers the sublimation temperature and this is effective for suppressing decomposition and change in quality of the sublimable substance. A suitable means to attain this purpose is to install the vacuum pump 13 at the end of collecting unit C. Depending upon the case, supply of an entraining gas such as nitrogen from the inlet of sublimating unit A helps to increase the rate of travel of the sublimable substance and the rate of sublimation.

The aforementioned explanation of the method for sublimation refining has covered the case where the feed contains the object sublimable substance and sublimable impurities showing lower sublimation temperature or lower boiling point than the object substance. In case the sublimable impurities boil higher than the object sublimable substance, the impurities are first collected in collecting unit B and the object sbulimable substance is collected in collecting unit C. Here, the collecting unit for the object sublimable substance is preferably made so that it can be heated by magnetic induction while the collecting unit for the impurities is not necessarily made so.

In the aforementioned mode of practice, the apparatus for sublimation refining used for explanation consists of sublimating unit A and a collecting unit comprising two zones differing from each other in temperature, namely, collecting unit B with its temperature control effected by electromagnetic induction heating and collecting unit C equipped with an ordinary cooling device, but this invention is not limited to this example.

For example, collecting unit B may contain two zones B1 and B2, which differ from each other in temperature and can be controlled at respective temperature by electromagnetic induction heating or the unit may contain three or more zones differing from one another in temperature. In the aforementioned case, providing a temperature gradient dropping approximately stepwise towards the downstream side in the sequence of sublimating unit A, collecting units B1 and B2 and collecting unit C makes it possible to condense fractionally the components of the sublimated gas according to their melting point in the collecting unit containing three zones differing from one another in temperature. Depending upon the case, it is possible to omit collecting unit C and let only the two or more collecting units controllable in temperature by electromagnetic induction heating separate fractionally the object substance and other components including impurities.

The diameter and length of the tubes to be used in the apparatus for sublimation refining can suitably be determined by the kind and amount to be treated of a sublimable substance. The apparatus of this invention for sublimation refining can treat sublimable substances in varying amounts, very small or large, and can also treat substances of varying sublimation temperature, from those sublimating at relatively low temperature on the order of 100° C. to those sublimating at high temperature on the order of 600° C. Moreover, reduction of the pressure of the refining apparatus makes it easy to carry out sublimation at low temperature and this procedure is suitable for refining unstable sublimable substances.

The apparatus of this invention for sublimation refining can be applied to refining by high-temperature distillation of those compounds which are difficult to refine by ordinary distillation; such a compound is distilled in the sublimating unit and collected as solid in the collecting unit which is kept at a temperature below its solidification point and, in this manner, the compound is evaporated and solidified rapidly with prevention of unnecessary overheating to yield the refined product of high purity.

EXAMPLES

This invention will be explained concretely below with reference to the examples.

Example 1

8-Hydroxyquinoline-aluminum complex (hereinafter referred to as Alq3), approximately 99% in purity, obtained by the reaction of 8 hydroxyquinoline and ammonium alum was refined by the apparatus for sublimation refining illustrated in FIG. 1.

A tube 2 which was prepared by plating the inside of a carbon steel tube, 50 mm in diameter and 100 mm in length, with molten aluminum was used for sublimating unit A and a tube 6 which was prepared by plating the inside of a carbon steel tube, 50 mm in inside diameter and 100 mm in length, with molten aluminum was used for sublimating unit B. The alternating current for electromagnetic induction was 200 V and 60 Hz and inverters were used for the temperature controllers 5 and 9.

To sublimating unit A was introduced 5 g of Alq3, the temperatures of the tubes 2 and 6 were controlled at 370° C. and 200° C. respectively, the periphery of collecting unit C was kept nearly at room temperature by contacting it with air the temperature of which was equal to room temperature and the refining apparatus was evacuated to 1 Torr (133 Pa) by the vacuum pump 13.

Refined Alq3 recovered from collecting unit B was 99.99% or more in purity and the yield was approximately 70%. A material regarded as decomposition product was recovered in 5% yield from collecting unit C.

Example 2

In an apparatus similar to the one in FIG. 1, sublimating unit A and collecting unit B were respectively made by inserting a quartz tube, 48 mm in outside diameter and 100 mm in length, as an inner tube into a carbon steel tube, 50 mm in diameter and 100 mm in length, or a tubular material generating heat by electromagnetic induction. This apparatus was used to refine by sublimation 5 g of Alq3 taken from the same lot as in Example 1. The temperatures of the tubes 2 and 6 were controlled respectively at 330° C. and 200° C. and the sublimation refining was carried out at 0.05 Torr (6.66 Pa) to yield refined Alq3 with a purity of 99.99% or more in 65% yield.

Example 3

In an apparatus similar to the one illustrated in FIG. 1, pyromellitic dianhydride with a purity of 98% prepared from tetramethylbenzene was refined by sublimation. A carbon steel tube, 50 mm in diameter and 100 mm in length, or a tubular material generating heat by electromagnetic induction was used to make sublimating unit A and collecting unit B and the inside of sublimating unit A, collecting unit B and collecting unit C was coated with enamel to prevent the metallic part from contacting pyromellitic dianhydride, pyromellitic acid, trimellitic acid, hemimellitic acid and the like. Sublimation refining of 10 g of the raw material pyromellitic dianhydride was carried out while controlling the temperatures of sublimating unit A and collecting unit B respectively at 180° C. and 100° C. and the pressure at 1–2 Torr (133–266 Pa) and introducing a small volume of nitrogen from the end of sublimating unit A in order to raise the rate of sublimation. The recovery of pyromellitic dianhydride as needle crystal was 82% and the purity was 99.9% or more. Tricarboxylic acids such as trimellitic acid were detected in a small amount of solid adhering to collecting unit C.

Example 4

In an apparatus similar to the one illustrated in FIG. 1, a carbon steel tube, 50 mm in diameter and 100 mm in length, or a tubular material generating heat by electromagnetic induction was used for sublimating unit A and collecting unit B and the inside of sublimating unit A, collecting unit B and collecting unit C was coated with TiN to prevent the metallic part from contacting sublimable substances. To sublimating unit A of this apparatus was introduced 5 g of N,N'-diphenyl-N,N'-bis(3-methylphenyl)-(1,1'-biphenyl)-4,4'-diamine (hereinafter referred to as TPD) and refined by sublimation to give 3 g of refined TPD while controlling the temperatures of sublimating unit A and collecting unit B respectively at 240° C. and 140° C. and the pressure at $1\times10^{-4}$ Torr (0.013 Pa). The purity (area %) determined by a high-performance liquid chromatograph was 99.0% for the raw material and 99.7% or more for the refined product.

Example 5

Carbazole with a purity of 85% separated from coal tar by such steps as distillation and crystallization was refined in an apparatus for sublimation refining similar to the one illustrated in FIG. 1.

A silicon carbide (SiC) tube, 30 mm in diameter and 100 mm in length, or a tubular material generating heat by electromagnetic induction was used for sublimating unit A and collecting unit B. A silicon carbide tube, 30 mm in diameter and 150 mm in length, was used for collecting unit C and the outer surface was cooled by air. To sublimating unit A was introduced 5 g of the raw material carbazole and sublimated while controlling the temperatures of sublimating unit A and collecting unit B respectively at 250° C. and 70° C. and the pressure at 30 Torr (4 kPa). The recovery of refined carbozole with an HPLC purity of 99% was 50%. Pitch containing unsublimated carbozole remained in sublimating unit A and anthracene, phenanthrene and the like were detected in the substances collected in collecting unit C.

INDUSTRIAL APPLICABILITY

According to the method of this invention for sublimation refining, the apparatus is coated with a material inert to sublimable substances and this prevents corrosion of the apparatus and contamination and change in quality of the product during sublimation of sublimable substances containing impurities by electromagnetic induction heating and gives the product of high purity in high yield.

What is claimed is:

1. An apparatus for sublimation refining which comprises a heat generating unit made of a material generating heat by electromagnetic induction, a sublimating unit and a collecting unit, respectively independently controllable in temperature by electromagnetic induction heating, wherein a material inert to a sublimable substance is used as a structural material for the inner surface or the inner tube of the sublimating unit and the collecting unit contacting said sublimable substance.

2. An apparatus for sublimation refining as described in claim 1 wherein the material generating heat by electromagnetic induction is a metallic material.

3. An apparatus for sublimation refining as described in claim 1 wherein the material generating heat by electromagnetic induction is a nonmetallic material.

4. An apparatus for sublimation refining as described in claim 1 wherein the sublimating unit and the collecting unit are made of a material of two layers or more containing a layer of a material generating heat by electromagnetic induction and an inner layer contacting said sublimable substance which comprises a material inert to said sublimable substance.

5. An apparatus for sublimation refining as described in claim 4 wherein the material inert to said sublimable substance is a material selected from the group consisting of metals, glasses, ceramics and fluoropolymers.

6. A method for sublimation refining in an apparatus for sublimation refining which apparatus comprises a heat generating unit made of a material generating heat by electromagnetic induction, and (b) a sublimating unit and a collecting unit, respectively independently controllable in temperature by electromagnetic induction heating, wherein a material inert to a sublimable substance such as metal, glass and ceramic is used as a structural material for the inner surface or the inner tube of the sublimating unit and the collecting unit contacting said sublimable substances, said method comprising (1) introducing a sublimable substance to the sublimating unit of the apparatus, (2) generating heat in the sublimating unit by electromagnetic induction thereby sublimating said sublimable substance, (3) introducing the sublimate to the collecting unit containing a zone controlled in temperature by electromagnetic induction heating, and (4) collecting the object sublimable substance.

7. A method for sublimation refining as described in claim 6 wherein the sublimable substance is a metal complex or an organic compound useful for an organic EL device material.

8. A method for sublimation refining as described in claim 7 wherein the inert material is glass selected from the group consisting of quartz glass, Pyrex, hard glass and enamel.

9. A method for sublimation refining as described in claim 7 wherein the sublimable substance is a metal complex or a metal complex useful for an organic EL device material and the inert material is a metal of the same kind as that of the metal complex.

10. A method for sublimation refining in an apparatus for sublimation refining which apparatus comprises (a) a heat generating unit made of a material generating heat by electromagnetic induction, and (b) a sublimating unit, a collecting unit containing plural zones of controlled temperature, and a vacuum pump arranged in sequence with the temperature in the sublimating unit and the collecting unit controlled to drop successively towards the downstream side, wherein the sublimating unit and the collecting unit are independently controllable in temperature by electromagnetic induction heating, and are made of a material of two layers or more containing a layer of a material generating heat by electromagnetic induction and an inner layer contacting a sublimable substance which comprises a material inert to said sublimable substance, said method comprising (1) introducing a sublimable substance selected from metal complexes and organic EL device materials to the sublimating unit of said apparatus for sublimation refining, (2) generating heat in the sublimating unit by electromagnetic induction thereby sublimating said sublimable substance, (3) introducing the sublimate to the collecting unit containing a zone controlled in temperature by electromagnetic induction heating and (4) collecting the object sublimable substance in the zone controlled at the specified temperature.

* * * * *